United States Patent
Gertzman et al.

(10) Patent No.: US 7,019,192 B2
(45) Date of Patent: Mar. 28, 2006

(54) COMPOSITION FOR FILLING BONE DEFECTS

(75) Inventors: Arthur A. Gertzman, Stony Point, NY (US); Moon Hae Sunwoo, Old Tappan, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 188 days.

(21) Appl. No.: 10/222,807

(22) Filed: Aug. 19, 2002

(65) Prior Publication Data

US 2002/0197242 A1    Dec. 26, 2002

Related U.S. Application Data

(63) Continuation-in-part of application No. 09/515,656, filed on Feb. 29, 2000, now Pat. No. 6,437,018, and a continuation-in-part of application No. 09/031,750, filed on Feb. 27, 1998, now Pat. No. 6,030,635, and a continuation-in-part of application No. 09/365,880, filed on Aug. 3, 1999, now abandoned.

(51) Int. Cl.
*A61K 35/32*   (2006.01)

(52) U.S. Cl. .................... 623/16; 514/772.3; 514/773; 514/777

(58) Field of Classification Search .............. 424/422; 623/16; 514/772.3, 773, 777
See application file for complete search history.

(56) References Cited

U.S. PATENT DOCUMENTS

| 4,172,128 A | | 10/1979 | Thiele et al. |
| 4,191,747 A | | 3/1980 | Scheicher |
| 5,073,373 A | | 12/1991 | O'Leary et al. |
| 5,290,558 A | | 3/1994 | O'Leary |
| 5,314,476 A | | 5/1994 | Prewett et al. |
| 5,356,629 A | * | 10/1994 | Sander et al. ............... 424/422 |
| 5,507,813 A | | 4/1996 | Dowd et al. |
| 5,510,418 A | * | 4/1996 | Rhee et al. ................ 525/54.2 |
| 5,707,962 A | * | 1/1998 | Chen et al. ................... 514/12 |
| 5,830,493 A | | 11/1998 | Yokota et al. |
| 6,294,187 B1 | * | 9/2001 | Boyce et al. ............... 424/422 |
| 6,689,747 B1 | | 2/2004 | Filvaroff et al. |

* cited by examiner

*Primary Examiner*—Thurman K. Page
*Assistant Examiner*—Marc C Fitzgerald
(74) *Attorney, Agent, or Firm*—John S. Hale; Gipple & Hale

(57) ABSTRACT

The invention is directed toward a formable bone composition for application to a bone defect site to promote new bone growth at the site which comprises a new bone growth inducing compound of demineralized lyophilized allograft bone particles. The particle size ranges from about 0.1 mm to about 1.0 cm and is mixed in a hydrogel carrier containing a sodium phosphate saline buffer, the hydrogel component of the carrier ranging from about 1.0 to 5.0% of the composition and a pH between 6.8–7.4 with one or more additives of a cellular material, growth factor, demineralized bone chips or mineralized bone chips.

22 Claims, No Drawings

COMPOSITION FOR FILLING BONE DEFECTS

RELATED APPLICATIONS

This is a continuation-in-part of U.S. patent application Ser. No. 09/515,656, filed Feb. 29, 2000 and issued into U.S. Pat. No. 6,437,018 on Aug. 20, 2002 and continuation-in-part of U.S. patent application Ser. No. 09/031,750, filed Feb. 27, 1998 and issued into U.S. Pat. No. 6,030,635 on Feb. 29, 2000 and continuation-in-part of U.S. patent application Ser. No. 09/365,880, filed Aug. 3,1999, now abandoned which is a continuation application of U.S. patent application Ser. No. 09/031,750.

FIELD OF INVENTION

The present invention is generally directed toward a surgical bone product and more specifically is a composition for filling bone defects using demineralized allograft bone particles, partially demineralized allograft bone particles or whole bone particles mixed in a fluid carrier having an isotonic phosphate buffer and a high molecular weight viscous excipient derived from the class of biomaterials known as hydrogels which contains cell material and/or growth factors.

BACKGROUND OF THE INVENTION

Surgical implants should be designed to be biocompatible in order to successfully perform their intended function. Biocompatibility may be defined as the characteristic of an implant acting in such a way as to allow its therapeutic function to be manifested without secondary adverse affects such as toxicity, foreign body reaction or cellular disruption.

Formable compositions are used to correct surgical defects that may be caused by trauma, pathological disease, surgical intervention or other situations where defects need to be managed in osseous surgery. It is important to have the defect filler in the form of a stable, viscous formable composition to facilitate the placement of the bone growth medium into the surgical site which is usually uneven in shape and depth. The surgeon will take the composition on a spatula or other instrument and trowel it into the site or take it in his/her fingers to shape the bone inducing material into the proper configuration to fit the site being corrected. It is also important that the defect filler be biocompatible and have the correct osmolality and pH and not cause any additional trauma at the surgical site.

Many products have been developed in an attempt to treat this surgical need for a biocompatible formable material. One such example is autologous bone particles or segments recovered from the patient. When removed from the patient, the segments or bone particles are wet and viscous from the associated blood. This works very well to heal the defect but requires significant secondary surgery resulting in lengthening the surgery, extending the time the patient is under anesthesia and increasing the cost. In addition, a significant increase in patient morbidity is attendant in this technique as the surgeon must take bone from a non-involved site in the patient to recover sufficient healthy bone, marrow and blood to perform the defect filling surgery. This leads to significant post-operative pain.

Another product group involves the use of inorganic materials to provide a matrix for new bone to grow at the surgical site. These inorganic materials include hydroxyapatite obtained from sea coral or derived synthetically. Either form may be mixed with the patient's blood and/or bone marrow to form a gel or a putty. Calcium sulfate or plaster of Paris may be mixed with water to similarly form a putty. These inorganic materials are osteoconductive but are bioinert and do not absorb or become remodeled into natural bone. They consequently remain in place indefinitely as a brittle, foreign body in the patient's tissue.

Allograft bone is a logical substitute for autologous bone. It is readily available and precludes the surgical complications and patient morbidity associated with autologous bone as noted above. Allograft bone is essentially a collagen fiber reinforced hydroxyapatite matrix containing active bone morphogenic proteins (BMP) and can be provided in a sterile form. The demineralized form of allograft bone is naturally both osteoinductive and osteoconductive. The demineralized allograft bone tissue is fully incorporated in the patient's tissue by a well established biological mechanism. It has been used for many years in bone surgery to fill the osseous defects previously discussed.

It is well known in the art that for several decades surgeons have used a patient's own blood as a vehicle in which to mix the patient's bone chips or bone powder, or demineralized bone powder so as to form a defect filling paste. Blood is a useful carrier because it is available from the bleeding operative site, is non-immunogenic to the patient and contains bone morphogenic proteins which facilitate wound healing through new bone growth. However, stored blood from other patients has the deficiencies that any blood transfusion would have; such as blood type compatibility, possibility of transmission of disease and unknown concentration of BMP which are to a great extent dependent upon the age of the donor.

While blood contains from forty percent (40%) to fifty percent (50%) cell mass, it is a satisfactory carrier for demineralized bone powder because it contains both mono- and polysaccharides which contribute to the blood viscosity and provide the bulk viscosity to the paste created by mixing the bone powder and blood. Specific monosaccharides in blood are glucose at a concentration of 60–100 mg/100 ml (0.1%) and polysaccharides such as hexose and glucosamine at approximately 0.1%. Glucuronic acid is also present at approximately 0.4–1.4 mg/100 ml (average 0.01%).

The problems inherent with using the patients blood as a carrier for demineralized bone powder are the difficulties of mixing the same at the operating site, the difficulty in obtaining a bone paste consistency which can be easily applied to the surgical area, the guesswork in mixing a usable composition at the site and the problem of having a bone paste or gel which will promote optimum bone replacement growth and not be carried away by the body fluids at the operation site or simply fall out of the bone defect site. In an attempt to solve these and other problems, there have been a number of other attempts using other alternative mixtures and compositions.

Demineralized allograft bone is usually available in a lyophilized or freeze dried and sterile form to provide for extended shelf life. The bone in this form is usually very coarse and dry and is difficult to manipulate by the surgeon. One solution to use such freeze dried bone has been provided in the form of a gel, GRAFTON®, a registered trademark of Osteotech Inc., which is a simple mixture of glycerol and lyophilized, demineralized bone powder of a particle size in the range of 0.1 cm to 1.2 cm (1000 microns to 12,000 microns) as is disclosed in U.S. Pat. No. 5,073,373.

GRAFTON works well to allow the surgeon to place the allograft bone material at the site. However, the carrier, glycerol has a very low molecular weight (92 Daltons) and is very soluble in water, the primary component of the blood which flows at the surgical site. Glycerol also experiences a marked reduction in viscosity when its temperature rises from room temperature (typically 22° C. in an operating room) to the temperature of the patient's tissue, typically 37° C. This combination of high water solubility and reduced viscosity causes the allograft bone material with a glycerol carrier to be "runny" and to flow away from the site almost immediately after placement; this prevents the proper retention of the bone material within the site as carefully placed by the surgeon.

These problems with GRAFTON gel have been attempted to be resolved by using a much larger particle size of allograft bone, specifically lamellae or slivers of bone created by milling or slicing the bone before mixing it with the glycerol carrier. This improves both the bulk viscosity and the handling characteristics of the mixture but still leaves the problem of the fast rate of dissipation of the carrier and some bone due to the solubility of the glycerol carrier. The larger particles of demineralized bone may also retard the development of new bone by the patient because the large bony lamellae do not pack as well as the smaller grainy particles of bone. This will leave more open space and could lengthen the time required to grow new bone and properly fill the defect. Another deficiency of using the bony lamellae is that the ends of the bony fragments are uneven and when packed into the surgical defect, uneven filaments of bone are left protruding out from the defect which can compromise the healing rate.

U.S. Pat. No. 5,290,558 discloses a flowable demineralized bone powder composition using an osteogenic bone powder with large particle size ranging from about 0.1 to about 1.2 cm. mixed with a low molecular weight polyhydroxy compound possessing from 2 to about 18 carbons including a number of classes of different compounds such as monosaccharides, disaccharides, water dispersible oligosaccharides and polysaccharides.

Hence, the advantages of using the smaller bone particle sizes as disclosed in the U.S. Pat. No. 5,073,373 gel patent were compromised by using bone lamellae in the shape of threads or filaments and retaining the low molecular weight glycerol carrier. This later prior art is disclosed in U.S. Pat. Nos. 5,314,476 and 5,507,813 and the tissue forms described in these patents are known commercially as the GRAFTON® Putty and Flex, respectively.

The use of the very low molecular weight glycerol carrier also requires a very high concentration of glycerol to be used to achieve the bulk viscosity. Glycerol and other similar low molecular weight organic solvents are toxic and irritating to the surrounding tissues.

U.S. Pat. No. 5,356,629 discloses making a rigid composition in the nature of a bone cement to fill defects in bone by mixing biocompatible particles preferably polymethylmethacrylate coated with polyhydroxyethylmethacrylate in a matrix selected from a group which lists hyaluronic acid to obtain a molded semi-solid mass which can be suitably worked for implantation into bone. The hyaluronic acid can also be utilized in monomeric form or in polymeric form preferably having a molecular weight not greater than about one million Daltons. It is noted that the nonbioabsorbable material which can be used to form the biocompatible particles can be derived from xenograft bone, homologous bone, autogenous bone as well as other materials. The bioactive substance can also be an osteogenic agent such as demineralized bone powder, in addition to morselized cancerous bone, aspirated bone marrow and other autogenous bone sources. The average size of the particles employed is preferably about 0.1 to about 3.0 mm, more preferably about 0.2 to about 1.5 mm, and most preferably about 0.3 to about 1.0 mm. It is inferentially mentioned but not taught that particles having average sizes of about 7,000 to 8,000 microns, or even as small as about 100 to 700 microns can be used. However, the biocompatible particles used in this reference are used in a much greater weight ranging from 35% to 70% by weight then that taught by the present invention. This is simply a cement used for implantation of hip prosthesis and is not used to promote bone growth.

U.S. Pat. No. 5,830,493 is directed toward a composite porous body (hyaluronic acid listed in a group of compounds) comprising a porous frame and a surface layer comprising a bioabsorbable polymer material formed on the surface. A bone morphogenetic protein (BMP) is carried on the surface and inside of the composite porous body. There is no demineralization of bone and the reference appears only to be relevant to show the addition of BMP to a bone forming graft.

Another attempt to solve the bone composition problem is shown in U.S. Pat. No. 4,172,128 which discloses demineralized bone material mixed with a carrier to reconstruct tooth or bone material by adding a mucopolysaccharide to a mineralized bone colloidal material. The composition is formed from a demineralized coarsely ground bone material, which may be derived from human bones and teeth, dissolved in a solvent forming a colloidal solution to which is added a physiologically inert polyhydroxy compound such as mucopolysaccharide or polyuronic acid in an amount which causes orientation when hydrogen ions or polyvalent metal ions are added to form a gel. The gel will be flowable at elevated temperatures above 35° C. and will solidify when brought down to body temperature. Example 25 of the patent notes that mucopolysaccharides produce pronounced ionotropic effects and that hyaluronic acid is particularly responsible for spatial cross-linking. Unfortunately this bone gel is difficult to manufacture and requires a premolded gel form.

U.S. Pat. No. 4,191,747 teaches a bone defect treatment with coarsely ground, denatured bone meal freed from fat and ground into powder. The bone meal is mixed with a polysaccharide in a solution of saline and applied to the bone defect site.

Another prior art product is the formulation of demineralized allograft bone particles in collagen. Both bovine and human collagen have been used for this application. Bovine collagen carries the risk of an immunogenic reaction by the recipient patient. Recently, it has been found that a disease of cattle, bovine spongioform encephalopathy (BSE) is transmitted from bovine tissue to humans. Thus, bovine tissue carries a risk of disease transmission and is not a desirable carrier for allograft tissue.

Human collagen is free of these animal based diseases. However, collagen absorbs slowly in the human body, particularly in a bony site with usually a low degree of vascularity. The slow absorption of collagen can delay the growth of new bone and result in the formation of scar tissue at the site. This could result in a non-bony healing and a result with much less tensile strength.

Accordingly, the prior art as embodied in the glycerol and other carrier based technology to deliver demineralized allograft bone to a surgical osseous site is replete with problems and only partially addresses the problems inherent in the correcting surgical defects.

SUMMARY OF THE INVENTION

The subject formulation is a complex mixture of osteoinductive bone particles and a viscous hydrogel based on a high molecular weight material with a sodium based phosphate buffer acting as a carrier or delivery vehicle for the osteoinductive particles which are mixed with living cells and/or cell elements or with a bone growth additive. The viscous formulation is designed to present the bone material and its bone morphogenetic proteins (BMP), and the macrostructure of the bone particles to serve both as an osteoconductive matrix and to signal the patient's tissue and cells to initiate the growth of new bone (osteoinduction). The formulation is used primarily in contact with bleeding bone. This condition is created either from trauma or a surgical procedure, that may involve drilling, sawing, grinding or scraping the bone to achieve a bleeding condition. In surgery, the bone is traumatized or surgically cut exposing blood capillaries, Haversian canals (micro-channels in the bone), periosteum (the protective tissue lining around bone), muscle and other structures in the surgical site. Bleeding at the site is considered a favorable condition to enhance healing of the wound site by bringing to the site the patient's own cytokines, i.e., proteins and other molecules which are the body's mechanism to carry out the healing process. Any interference with the blood cell mechanism would be considered non-biocompatible and an adverse outcome.

In order for the bone material to be osteoinductive, interference either from the traumatized cells or the formulation must be at a minimum, i.e., a biocompatible condition should be established and maintained. Several specific properties have been established in the formulation to create a functional and therapeutic material. These properties pertain to both physical characteristics and to the achieving of a biocompatible or physiologically friendly condition.

It is an object of the invention to utilize bone material in a particle size that is useful to achieve the malleability characteristics that maximizes the amount of bone in the formulation.

It is an additional object of the invention to use a non toxic aqueous solution carrier with a sodium phosphate buffer for the bone particles to present the composition in a state of physiological osmolality at the wound site.

It is also an object of the invention to create a bone defect material which can be easily handled by the physician and does not degenerate when contacting blood flow at the surgical site.

It is another object of the invention to create a bone defect material which uses cellular material such as living cells and cell elements.

It is still another object of the invention to create a bone defect material which has a stable viscosity from 22° to 37° C.

It is an additional object of the invention to create a bone defect material with an isotonic pH.

It is yet another object of the invention to use a growth factor in the bone composition.

DESCRIPTION OF THE INVENTION

The present invention is directed towards a demineralized or partially demineralized bone particle composition to heal bone defects.

A formable composition with a useful bulk viscosity has been achieved by using a soluble biomaterial, hydrogel. The balance of the carrier formulation is an aqueous solution and preferably includes the addition of a material component, namely, a sodium based phosphate buffer in a sterile saline or salt carrying water which avoids the toxic problems with the high concentrations of the low molecular weight organic solvents of the prior art.

The particle size of demineralized, lyophilized, allograft bone when mixed with high molecular weight stable viscosity hydrogels in a suitable carrier produces a formable composition with clinically useful bone inducing properties. The formable property permits the surgeon to shape the bone composition to exactly fit the surgical defect. Manipulation of the "lump" of formable bone composition may be done without it sticking to the gloves of the surgeon, behaving somewhat like a wet clay used in sculpting.

It is an important aspect of the present invention that the implant matrix must remain at the wound site and not be washed away by the flowing blood and other fluids brought to the site by the healing mechanism. This is achieved by both the viscous and hydrogel state of the carrier. While viscous, the aqueous carrier is a high molecular weight macromolecule held together with water linkages (hydrogen bonds) and is not readily dissolved and washed away by the blood and fluids at the wound site.

Thus, the therapeutic formable bone composition will not be dissipated by being washed away and will be present to be osteoinductive.

The amount of demineralized bone material (DBM) is maximized to achieve the optimum balance of osteoinductivity and physical handling properties. Too much matrix bone may create a gritty or sandy condition in which the DBM is not ideally enclosed by the surrounding viscous matrix and the DBM bone particles would be too easily washed away. Conversely, if the bone concentration is too low, the osteoinductivity would be less than optimum. Bone concentration in the composition is in the range of about 20% to about 50%.

The types of demineralized bone used in the invention are cortical and corticocancellous bone particles. However other bone materials such as partially demineralized chips or granules having the particle size of 0.1 mm to 1.0 cm or non demineralized chips or granules derived from cortical bone having the particle size of 0.1 mm to 1.0 cm can be added to the demineralized bone. Similarly living cells and cell elements and/or growth factors can be added to the composition.

The primary role of a carrier is to serve as a delivery vehicle. The bulk viscosity of the carrier achieves the design goal of good handling properties by balancing the molecular weight and concentration of the hydrogel used in the formulation. For example, a very high molecular weight hydrogel would use a lower concentration compared to a formulation in which the hydrogel molecular weight was considerably lower with a higher concentration used to achieve the same bulk viscosity. The nominal formulation uses a 660,000 Dalton molecular weight hydrogel (sodium hyaluronate, or HA). This HA material is used at a 1–5% concentration in water or phosphate buffered saline to achieve the bulk viscosity required for the formulation.

If the balance of molecular weight and concentration were not optimized, the results would be a runny, excessively fluid formulation that would not stay at the surgical site. While Hydrogel molecular weights as low as 150,000 Dalton with a concentration as high as about 10–15% would give a good bulk viscosity, concentrations with corresponding viscosity above this level cannot be filtered to achieve sterility required by a surgical implant. Guidelines for sterility require a statistical assurance of no more surviving microorganisms than one in one million. This cannot be achieved above a concentration of about 5–6% hydrogel of a molecular weight of 660,000 to 700,000 Daltons. Very much higher concentrations would result in a semi solid not having desirable handling properties as it would lose the desirable malleability required for a defect filling formulation.

The carriers for the formable bone composition are preferably taken from higher molecular weight hydrogels such as: 1) Sodium Hyaluronate $6.6\times10^5$–$2.6\times10^6$ Daltons and its derivatives; and 2) Lesser molecular weight hydrogels such as 3) Chitosan about 10,000 to 300,000 Daltons; 4) Sodium Alginate about 10,000 to 300,000 Daltons; 5) Dextran about 20,000 to 40,000 Daltons; 6) carboxymethylcellulose (CMC) about 20,000 to 40,000 Daltons and 7) hydroxypropylmethylcellulose (HPMC) about 20,000 to 40,000 Daltons. Other non hydrogel substances which can be used are collagen.

The natural condition for blood plasma as well as synovial fluid, cerebrospinal fluid, aqueous humor (fluid within the globe of the eye) is at a pH of 7.3–7.4 (reference, *Principles of Biochemistry,* Chapters 34 & 35; White, Handler and Smith, McGraw Hill, N.Y., 1964). At very slight changes in pH, blood cells will shift their equilibrium of hemoglobin. This hemoglobin concentration will change over the small pH range of 7.3 to 7.7 (White et al p. 664). In addition, at significantly lower pH values in the acidic range, protein molecules will denature, i.e., degrade. Thus, it is important to maintain any surgical implant which is intimate contact with blood at a biocompatible condition of about pH 7.2–7.4.

It is important to note that the body has many complex and redundant mechanisms to maintain its biochemical balance. The blood pH can be adjusted by several means to its normal, physiologic pH. Hence the presence of a non-physiologic material at the site of a bleeding bone wound will eventually be overcome and any non-biocompatible condition will return to normal pH. The preferred formulation will start out and maintain pH within the range of 6.8 to 7.4 without stressing the body's biochemical mechanisms when the bone composition material is applied at the wound site.

In achieving physiologic pH, the formulation uses a phosphate buffer based on an aqueous system of the two phosphate anions, $HPO_4^{-2}$ and $H_2PO_4^{-1}$. This buffer system is used both to neutralize the acid used to demineralize the bone and to buffer the sodium hyaluronate viscous hydrogel carrier. It is important to neutralize the acid (hydrochloric acid) used to demineralize the bone so as to assure that there is no residue of this very strong acid which could overwhelm the buffering capacity of the phosphate system used to buffer the sodium hyaluronate carrier.

The pH is adjusted to the physiologic a range of 6.8 to 7.4 pH or preferably 7.2–7.4 pH by using either or both of dibasic sodium phosphate or monobasic sodium phosphate and adjusting the solution with saline, i.e., a sodium chloride solution. The sodium chloride is chosen instead of only water so as to control the final osmolality of the formulation to preclude dehydration of the surrounding cells.

The buffer introduced contains sodium and phosphate ions which will remain in solution due to the high solubility of sodium phosphate. Calcium ions in the extracellular fluid will react with the phosphate ions to result in the precipitation of insoluble calcium phosphate salt. More phosphate ions will ionize from the associated state of the phosphate buffer to introduce more phosphate ions that will, in turn react with more calcium and precipitate yet more insoluble calcium phosphate. The calcium phosphate will deposit at the wound site where the buffered formulation was placed by the surgeon. This results in an increase in the presence of calcium at the wound site. The bone regeneration mechanism will utilize calcium starting 7–10 days after the wound starts healing by the well-known osteochondral healing mechanism. Hence, the selection of the sodium phosphate buffer to achieve the physiologic pH provides a means to increase the calcium concentration in the precise location where calcium will be needed to grow new bone.

Thus, the invention induces the presence of soluble calcium at the bone defect site. This will encourage new bone growth through the normal biochemical mechanism. Soluble calcium can be attracted to the surgical site by using a sodium phosphate buffer of pH 6.8–7.2 in lieu of isotonic saline. The phosphate buffer attracts calcium cations to the site from the surrounding healthy bone and creates an equilibrium concentration of the calcium precisely at the site of healing where it is most desirable to grow new bone.

It is a well known principal of physiology that osmotic pressure must be maintained within a narrow range to assure healthy conditions for the many cell types present in normal or surgically wounded cells. The condition of normal osmotic pressure is referred to as an isotonic state and is quantified in humans by the value of about 300 mOsmol/Kg. The sodium hyaluronate (HA) formulation is buffered to isotonic conditions using sodium chloride as the ionic salt to supplement the sodium phosphate. Were the sodium hyaluronate formulation to be buffered without the supplemental saline, the final hydrogel would only reach an osmolality of less than 50 mOsmol/Kg.

At this low osmolality, the extra cellular environment at the wound site would be in a state of hypotonicity and result in the inflow of large quantities of water to the cells and blood cells at the wound site to normalize the osmotic pressure. This will result in a greater than optimum degree of hydration of the cells and inhibit wound healing in general and bone growth in particular. Hemolysis may occur due to excess fluid in the cells.

Sodium hyaluronate in the form of the sodium salt is generally described as an acid mucopolysaccharide. It is envisioned that suitable amounts of bone morphogenic proteins (BMP) can be added to either the gel or putty at any stage in the mixing process to induce accelerated healing at the bone site. BMP directs the differentiation of pluripotential mesenchymal cells into osteoprogenitor cells which form osteoblasts. The ability of freeze dried demineralized cortical bone to transfer this bone induction principle using BMP present in the bone is well known in the art. However, the amount of BMP varies in the bone depending on the age of the bone donor and the bone processing. Sterilization is an additional problem in processing human bone for medical use as boiling, autoclaving and irradiation over 2.0 mrads is sufficient to destroy or alter the BMP present in the bone matrix.

A product with satisfactory formability and handling properties could have a sodium hyaluronate molecular weight ranging from 690,0000 to 1,200,000 Daltons with a sodium hyaluronate concentration ranging from 0.75–2.0% with a bone concentration ranging from 25–27% with a particle size of 100–820 microns. This resulted in HA solution viscosities ranging from about 1,800 cps to about 13,000 cps. It was also found that a putty product with optimal formability and handling properties would have a molecular weight ranging from 690,000 to 1,200,000 Daltons with a sodium hyaluronate concentration ranging from 2.0–4.5% with a bone concentration ranging from 30–33% with a particle size of 100–820 microns. This resulted in HA solution viscosities ranging from about 6,000 cps to about 275,000 cps. Less molecular weight hydrogels are used by increasing the percentage of hydrogel added to the carrier. As an example, the aforenoted chitosan and sodium alginate at a range of 100,000 to 3,000,000 Daltons molecular weight are used in a concentration of 15% to 20% while the lower weight Dextran, CMC and HPMC in a concentration of 15% to 30%. Osmolality ranges from 280 to 320.

Additives which are beneficial to bone growth and are added into the formable composition are living cells and cell elements such as chondrocytes, red blood cells, white blood cells, platelets, blood plasma, bone marrow cells, mesenchymal stem cells, pluripotential cells, osteoblasts, osteoclasts, and fibroblasts, epithelial cells, and endothelial cells. These cells or cell elements or combinations of the same are present at a concentration of $10^5$ to $10^8$ per cc of carrier and are added into the composition at time of surgery.

Growth factor additives which can be used in the present invention either at the time of packaging or at surgery depending on the stability of the growth factor are transforming growth factor (TGF-beta), insulin growth factor (IGF-1); platlet derived growth factor (PDGF), vascular endothelial growth factor (VEGF), fibroblast growth factor (FGF) (numbers 1–23), osteopontin, growth hormones such as somatotropin cellular attractants and attachment agents.

Any number of medically useful substances can be used in the invention by adding the substances to the composition at any steps in the mixing process or directly to the final composition. Such substances include collagen and insoluble collagen derivatives, hydroxy apatite, tricalcium phosphate and soluble solids and/or liquids dissolved therein.

Also included are antiviricides such as those effective against HIV and hepatitis; antimicrobial and/or antibiotics such as erythromycin, bacitracin, neomycin, penicillin, polymyxin B, tetracycline, viomycin, chloromycetin and streptomycin, cefazolin, ampicillin, azactam, tobramycin, clindamycin and gentamycin.

It is also envisioned that amino acids, peptides, vitamins, co-factors for protein synthesis; hormones; endocrine tissue or tissue fragments; synthesizers; enzymes such as collagenase, peptidases, oxidases; polymer cell scaffolds with parenchymal cells; angiogenic drugs and polymeric carriers containing such drugs; collagen lattices; biocompatible surface active agents, antigenic agents; cytoskeletal agents; cartilage fragments, In the following examples the molecular weight of the various carrier components used is as follows:

EXAMPLE I

A formable putty of 2% solution sodium hyaluronate in isotonic saline with 250–420 micron cortical allograft bone demineralized powder @ 30%.

502 milligrams of freeze dried demineralized cortical allograft bone of particle size ranging from 250–420 microns was mixed into 1,170 milligrams of a 2% solution of sodium hyaluronate in isotonic saline with a phosphate buffer. The bone component is added to achieve a bone concentration of 30% (w/w). The mixture was well stirred and allowed to stand for 2–3 hours at room temperature to provide a malleable putty with excellent formability properties.

EXAMPLE II

A flowable gel of 250–420 micron particle size demineralized cortical allograft bone granules in a 1% solution of sodium hyaluronate at a 25% (w/w) of bone content.

503 milligrams of allograft freeze dried demineralized cortical bone was mixed into 1,502 milligrams of a 1% solution of sodium hyaluronate having a viscosity ranging from 2,000 cps to 6,000 cps in an aqueous solution of a sodium chloride based phosphate buffer. The mixture at room temperature provided a flowable gel.

EXAMPLE III

A flowable gel of 250–420 micron particle size demineralized cortical allograft granules in a 1% solution of sodium hyaluronate at a 30% (w/w) of bone content.

501 milligrams of allograft freeze dried demineralized cortical bone was mixed into 1,167 milligrams of a 1% solution of sodium hyaluronate in isotonic saline phosphate buffer. The bone component is added to achieve a bone concentration of 30% (w/w). The mixture was well stirred and allowed to stand for 2–3 hours at room temperature. This provided a flowable gel.

EXAMPLE IV

A flowable gel of 420–850 micron particle size demineralized cortical allograft granules in a 1% solution of sodium hyaluronate at a 25% (w/w) of bone content.

501 milligrams of allograft freeze dried demineralized cortical bone was mixed into 1,501 milligrams of a 1% solution of sodium hyaluronate in isotonic saline phosphate buffer. The bone component is added to achieve a bone concentration of 25% (w/w). The mixture was well stirred and allowed to stand for 2–3 hours at room temperature. This provided a flowable gel.

EXAMPLE V

A malleable putty of 250–710 micron particle size demineralized cortical allograft granules in a 4.4% solution of sodium hyaluronate at a 30% (w/w) of bone content. 90 grams of freeze-dried demineralized cortical allograft bone were mixed into 210 grams of a 4.4% solution of sodium hyaluronate (660,000 Daltons) in phosphate buffered saline with pH 7.3, viscosity of 207,000 cps and osmolality of 337 mOsmol/Kg. The bone component was added to achieve a bone concentration of 30% (w/w). The mixture at room temperature provided a malleable putty.

EXAMPLE VI

A flowable gel of 250–710 micron particles of demineralized cortical allograft granules in a 1.9% solution of sodium hyaluronate at 25% (w/w) of bone content.

75 g of freeze-dried demineralized cortical allograft bone was mixed into 225 g of 1.9% solution of sodium hyaluronate (660,000 Daltons) in phosphate buffered saline with pH 7.3, viscosity of 8,700 cps and osmolality of 314 mOsmol/Kg. The bone component was added to achieve a bone concentration of 25% (w/w). The mixture at room temperature provided a flowable gel.

A flowable gel can be made up of about 25–30% demineralized bone powder (particle size in a range of 250–850 microns) mixed into a high molecular weight hydrogel carrier in solution, such as 1% to 2% sodium hyaluronate, with greater ranges for chitosan and sodium alginate such as 5% to 20% and still greater ranges for Dextran, CMC and HPMC such as 15% to 30%.

A flowable putty can be made up of about 30–35% demineralized bone powder (particle size in a range of 250–850 microns) mixed into a high molecular weight hydrogel carrier in solution, such as 4% to 5% sodium hyaluronate, with greater percentage ranges for chitosan and sodium alginate such as 10% to 20% and still greater ranges for Dextran, CMC and HPMC such as 20% to 30%.

Osmolality for all compositions ranged from 280 to 320 mOsmol/Kg.

In examples 1–6 living cells and cell elements such as chondrocytes, red blood cells, white blood cells, platelets, blood plasma, bone marrow cells, mesenchymal stem cells,

What we claim is:

1. A sterile formable bone composition for application to a bone defect site to promote new bone growth at the site comprising demineralized osteoinductive and osteoconductive bone particles in an aqueous carrier solution, said bone particles are alloaraft bone ranging from about 100 microns to about 850 microns in size at a concentration ranging from 20% to 35% by weight of the composition, the carrier comprising a hydrogel component of sodium hyaluronate or its derivatives in a phosphate buffered aqueous solution, said hydrogel ranging from about 1.0% to about 5.0% by weight of the aqueous carrier solution and cellular material taken from a group consisting of living cells, cell elements such as red blood cells, white blood cells, platelets, blood plasma, pluripotential cells, osteoblasts, osteoclasts, and fibroblasts, epithelial cells, and endothelial cells present at a concentration of $10^5$ to $10^8$ per cc of the carrier, said hydrogel component having a high molecular weight ranging from about six hundred sixty thousand to three million Daltons with a stable viscosity at a temperature ranging from about 22° C. to about 37° C. and said composition having a pH ranging from about 6.8 to about 7.4

2. A sterile formable bone composition as claimed in claim 1 including growth factor additive added to said composition, said growth factor comprising one or more of a group consisting of transforming growth factor (TGF-beta), insulin growth factor (IGF-1); platlet derived growth factor (PDGF), vascular endothelial growth factor (VEGF), fibroblast growth factor (FGF) (numbers 1–23), osteopontin, growth hormones such as somatotropin celiular attractants and attachment agents.

3. A sterile formable bone composition as claimed in claim 1 including growth factor additive added to said composition comprising one or more of a group consisting of fibroblast growth factor (FGF) (numbers 1–23) in the amount of 2–4 milligrams in 10 cc of carrier solution.

4. A sterile formable bone composition as claimed in claim 1 wherein said composition includes an additive collagen and insoluble collagen derivatives.

5. A sterile formable bone composition as claimed in claim 1 wherein said composition includes the addition of calcium hydroxyapatite at a concentration of 20–35% measured as calcium.

6. A sterile formable bone composition as claimed in claim 1 wherein said composition includes bone chips taken from a group consisting of partially demineralized chips and non demineralized chips having a particle size ranging from 0.1 mm to 1.0 cm which are added to said viscous carrier at a concentration of about 5% to about 25%.

7. A sterile formable bone composition for application to a bone defect site to promote new bone growth at the site comprising a demineralized or vartially demineralized osteoinductive and osteoconductive bone particles in an aqueous carrier solution, said bone particles ranging from about 100 microns to about 850 microns in size at a concentration ranging from about 20% to about 35% by weight of the composition the carrier comprising a hydrogel component of sodium hyaluronate or its derivatives in a phosphate buffered aqueous solution, said hydrogel ranging from about 1.0% to about 5.0% by weight of the aqueous carrier solution and said hydrogel component having a high molecular weight ranging from about six hundred sixty thousand to three million Daltons with a stable viscosity at a temperature ranging from about 22° C. to about 37° C., said composition having a pH ranging from about 6.8 to about 7.4 and a growth factor additive added to said composition, said growth factor comprising one or more of a group consisting of transforming growth factor (TGF-beta), insulin growth factor (IGF-1); platlet derived growth factor (PDGF), vascular endothelial growth factor (VEOF), fibroblast growth factor (FGF) (numbers 1–23), osteopontin, growth hormones such as somatotropin cellular attractants and attachment agents.

8. A sterile formable bone composition as claimed in claim 7 including a cellular material taken from a group consisting of living cells and cell elements such as chondrocytes, red blood cells, white blood cells, platelets, blood plasma, bone marrow cells, mesenchymal stem cells, pluripotential cells, osteoblasts, osteoclasts, and fibroblasts, epithelial cells, and endothelial cells. These cells or cell elements or combinations of the same are present at a concentration of $10^5$ to $10^8$ per cc of the carrier.

9. A sterile formable bone composition as claimed in claim 7 wherein said composition includes an additive collagen and insoluble collagen derivatives.

10. A sterile formable bone composition as claimed in claim 7 wherein said composition includes the addition of calcium hydroxyapatite at a concentration of 20–35% measured by weight of the compostion.

11. A sterile formable bone composition as claimed in claim 7 wherein said bone particles are taken from a group consisting of allograft bone, cortical allograft bone, corticalcancellous bone, cancellous bone, autologous bone and xenograft bone.

12. A sterile formable bone composition as claimed in claim 7 wherein said composition includes bone chips taken from a group consisting of partially demineralized chips and fully mineralized chips having a particle size ranging from 0.1 mm to 1.0 cm which are added to said viscous carrier at a concentration of about 5% to about 25%.

13. A sterile formable bone composition for application to a bone defect site to promote new bone growth at the site comprising a demineralized osteoinductive and osteoconductive bone particles in an aqueous carrier solution, the bone particles being added to a viscous carrier at a concentration ranging from about 20% to about 50% (w/w), the carrier comprising a hydrogel taken from a group consisting of Dextran, carboxymethylcellulose (CMC) and hydroxypropylmethylcellulose (HPMC) in a phosphate buffered aqueous solution, said hydrogel ranging from about 15% to about 30% by weight of the aqueous carrier solution and said hydrogel component having a molecular weight ranging from twenty thousand to forty thousand Daltons with a stable viscosity at a temperature ranging from about 22° C. to about 37° C. and said composition having a pH ranging from about 6.8 to about 7.4 and a growth factor additive added to said composition, said growth factor comprising one or more of a group consisting of transforming growth factor (TGF-beta), insulin growth factor (IGF-1); platlet derived growth factor (PDGF), vascular endothelial growth factor (VEGF), fibroblast growth factor (FGF) (numbers 1–23), osteopontin, growth hormones such as somatotropin cellular attractants and attachment agents.

14. A sterile formable bone composition as claimed in claim 13 including a cellular material additive taken from a group consisting of living cells and cell elements such as chondrocytes, red blood cells, white blood cells, platelets, blood plasma, bone marrow cells, mesenchymal stem cells, pluripotential cells, osteoblasts, osteoclasts, and fibroblasts, epithelial cells, and endothelial cells, said cells or cell elements or combinations of the same being present at a concentration of $10^5$ to $10^8$ per cc of the carrier.

15. A sterile formable bone composition for application to a bone defect site to promote new bone growth at the site comprising demineralized osteoinductive and osteoconductive bone particles an aqueous carrier solution, the bone particles being added to a viscous carrier at a concentration ranging from about 20% to about 50% (w/w), the carrier comprising a hydrogel taken from a group consisting of Dextran, carboxymethylcellulose (CMC) and hydroxypropyhnethylcellulose (HPMC) in a phosphate buffered aqueous solution, said hydrogel ranging from about 15% to about 30% by weight of the aqueous carrier solution and cellular material taken from a group consisting of living cells, cell elements such as red blood cells, white blood cells, platelets, blood plasma, pluripotential cells, osteoblasts, osteoclasts, and fibroblasts, epithelial cells, and endothelial cells present at a concentration of $10^5$ to $10^8$ per cc of the carrier, said hydrogel component having a molecular weight ranging twenty thousand to forty thousand Daltons with a stable viscosity and said composition having a pH ranging from about 6.8 to about 7.4

16. A sterile formable bone composition as claimed in claim 15 including growth factor additive added to said composition, said growth factor comprising one or more of a group consisting of transforming growth factor (TGF-beta), insulin growth factor (IGF-1); platlet derived growth factor (PDGF), vascular endothelial growth factor (VEGF), fibroblast growth factor (FGF) (numbers 1–23), osteopontin, growth hormones such as somatotropin cellular attractants and attachment agents.

17. A sterile formable bone composition as claimed in claim 15 including growth factor additive added to said composition comprising one or more of a group consisting of fibroblast growth factor (FGF) (numbers 1–23) in the amount of 2–4 milligrams in 10 cc of carrier solution.

18. A sterile formable bone composition for application to a bone defect site to promote new bone growth at the site comprising a demineralized osteo inductive and osteoconductive bone particles in an aqueous carrier solution, the bone particles being added to a viscous carrier at a concentration ranging from 5–50% (w/w), the carrier comprising a hydrogel taken from a group consisting of chitosan and sodium alginate in a phosphate buffered aqueous solution, said hydrogel ranging from about 5.0% to about 20.0% by weight of the aqueous carrier solution and said hydrogel component having a molecular weight ranging from ten thousand to three hundred thousand Daltons with a stable viscosity at a temperature ranging from about 22° C. to about 37° C. and said composition having a pH ranging from about 6.8 to about 7.4 and a growth factor additive added to said composition, said growth factor comprising one or more of a group consisting of transforming growth factor (TGF-beta), insulin growth factor (IGF-1); platlet derived growth factor (PDGF), vascular endothelial growth factor (VEGF), fibroblast growth factor (FGF) (numbers 1–23), osteopontin, growth hormones such as somatotropin cellular attractants and attachment agents.

19. A sterile formable bone composition as claimed in claim 18 including a cellular material additive taken from a group consisting of living cells and cell elements such as chondrocytes, red blood cells, white blood cells, platelets, blood plasma, bone marrow cells, mesenchymal stem cells, pluripotential cells, osteoblasts, osteoclasts, and fibroblasts, epithelial cells, and endothelial cells. These cells or cell elements or combinations of the same are present at a concentration of $10^5$ to $10^8$ per cc of the carrier.

20. A sterile formable bone composition for application to a bone defect site to promote new bone growth at the site comprising demineralized osteoinductive and osteoconductive bone particles in an aqueous carrier solution, the bone particles being added to a viscous carrier at a concentration ranging from 5–50% (w/w), the carrier comprising a hydrogel taken from a group consisting of chitosan and sodium alginate in a phosphate buffered aqueous solution, said hydrogel ranging from about 5.0% to about 20.0% by weight of the aqueous carrier solution and cellular material taken from a group consisting of living cells, cell elements such as red blood cells, white blood cells, platelets, blood plasma, pluripotential cells, osteoblasts, osteoclasts, and fibroblasts, epithelial cells, and endothelial cells present at a concentration of $10^5$ to $10^8$ per cc of the carrier, said hydrogel component having a molecular weight ranging from ten thousand to three hundred thousand Daltons with a stable viscosity and said composition having a pH ranging from about 6.8 to about 7.4

21. A sterile formable bone composition as claimed in claim 20 including growth factor additive added to said composition, said growth injector comprising one or more of a group consisting of transforming growth factor (TGF-beta), insulin growth factor (IGF-1); platlet derived growth factor (PDGF), vascular endothelial growth factor (VEGF), fibroblast growth factor (FGF) (numbers 1–23), osteopontin, growth hormones such as somatotropin cellular attractants and attachment agents.

22. A sterile formable bone composition as claimed in claim 20 including growth factor additive added to said composition comprising one or more of a group consisting of fibroblast growth factor (FGF) (numbers 1–23) in the amount of 2–4 milligrams in 10 cc of carrier solution.

* * * * *

UNITED STATES PATENT AND TRADEMARK OFFICE
CERTIFICATE OF CORRECTION

| | | |
|---|---|---|
| PATENT NO. | : 7,019,192 B2 | Page 1 of 1 |
| APPLICATION NO. | : 10/222,807 | |
| DATED | : March 28, 2006 | |
| INVENTOR(S) | : Gertzman and Sunwoo | |

It is certified that error appears in the above-identified patent and that said Letters Patent is hereby corrected as shown below:

Column 11,
Line 21, the word "alloagraft" should read --allograft--.
Line 45, the word "celiular" should read --cellular--.
Line 67, the word "vartially" should read --partially--.

Column 13,
Lines 21-22, the word "hydroxypropyhnethylcellulose" should read --hydroxypropylmethylcellulose--.
Line 50, the words "osteo inductive" should read --osteoinductive--.

Signed and Sealed this

Eleventh Day of July, 2006

JON W. DUDAS
*Director of the United States Patent and Trademark Office*